United States Patent [19]
Hazlehurst et al.

[11] Patent Number: 6,003,020
[45] Date of Patent: Dec. 14, 1999

[54] INTELLIGENT PROFILING SYSTEM

[75] Inventors: Brian L. Hazlehurst, Portland; Scott M. Burke, Corvallis, both of Oreg.

[73] Assignee: Sapient Health Network, Portland, Oreg.

[21] Appl. No.: 09/137,622

[22] Filed: Aug. 21, 1998

Related U.S. Application Data

[60] Provisional application No. 60/064,398, Oct. 30, 1997.

[51] Int. Cl.[6] ................................................. G06F 15/18
[52] U.S. Cl. .......................... 706/11; 706/52; 706/924; 600/300
[58] Field of Search ...................... 706/11, 12, 924, 706/52; 705/3; 128/924; 600/300

[56] References Cited

U.S. PATENT DOCUMENTS

| | | | |
|---|---|---|---|
| 4,622,013 | 11/1986 | Cerchio | 434/118 |
| 4,839,822 | 6/1989 | Dormond et al. | 706/11 |
| 5,103,498 | 4/1992 | Lanier et al. | 706/11 |
| 5,239,617 | 8/1993 | Gardner et al. | 706/11 |
| 5,299,121 | 3/1994 | Brill et al. | 600/301 |
| 5,477,447 | 12/1995 | Luciw et al. | 706/11 |
| 5,485,544 | 1/1996 | Nonaka et al. | 706/11 |
| 5,517,405 | 5/1996 | McAndrew et al. | 706/45 |
| 5,560,011 | 9/1996 | Uyama | 706/11 |
| 5,672,154 | 9/1997 | Sillen et al. | 604/50 |
| 5,799,292 | 8/1998 | Hekmatpour | 706/11 |
| 5,823,949 | 10/1998 | Goltra | 600/300 |
| 5,835,900 | 11/1998 | Fagg, III et al. | 706/11 |

OTHER PUBLICATIONS

L. Frisch and A.R. Wenner, "Automated Telephone Interviewing to Improve Health Care Access," Proc. Twelfth Int'l. Symp. on the Creation of Electronic Health Record System and Global Conf. on Patient Cards, vol. 2, pp. 529–535, May. 1996.

G. Carenini, et al., "An Information–Based Bayesian Approach to History Taking," 5th Conf. on Artificial Intelligence in Medicine Europe, pp. 129–138, Jun. 1995.

*Primary Examiner*—Robert W. Downs
*Attorney, Agent, or Firm*—Marger Johnson & McCollom, P.C.

[57] ABSTRACT

An Intelligent Profiling Engine system contains a knowledge base and form base in which domain knowledge, forms, filters, rules, and clocks are represented. The system profiles users by presenting forms containing questions to users via multiple communication channels. Forms are selected based upon the results of utilizing filters, rules, and clocks to identify target populations of users. Filters, rules, and clocks also specify what information is important with respect to each user and how frequently information about each user must be refreshed. Liaisons present forms to users, store answers in a user data tank, and deliver benefits to users as a reward for answering questions. The system maximizes the utility of information gathered from users over time according to form weights. Thus, the invention is an automated profiling scheme.

26 Claims, 6 Drawing Sheets

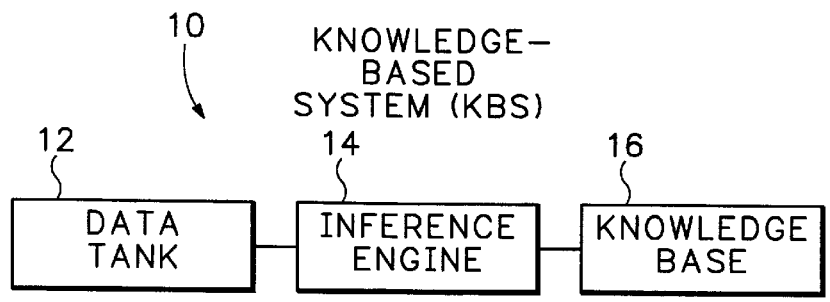
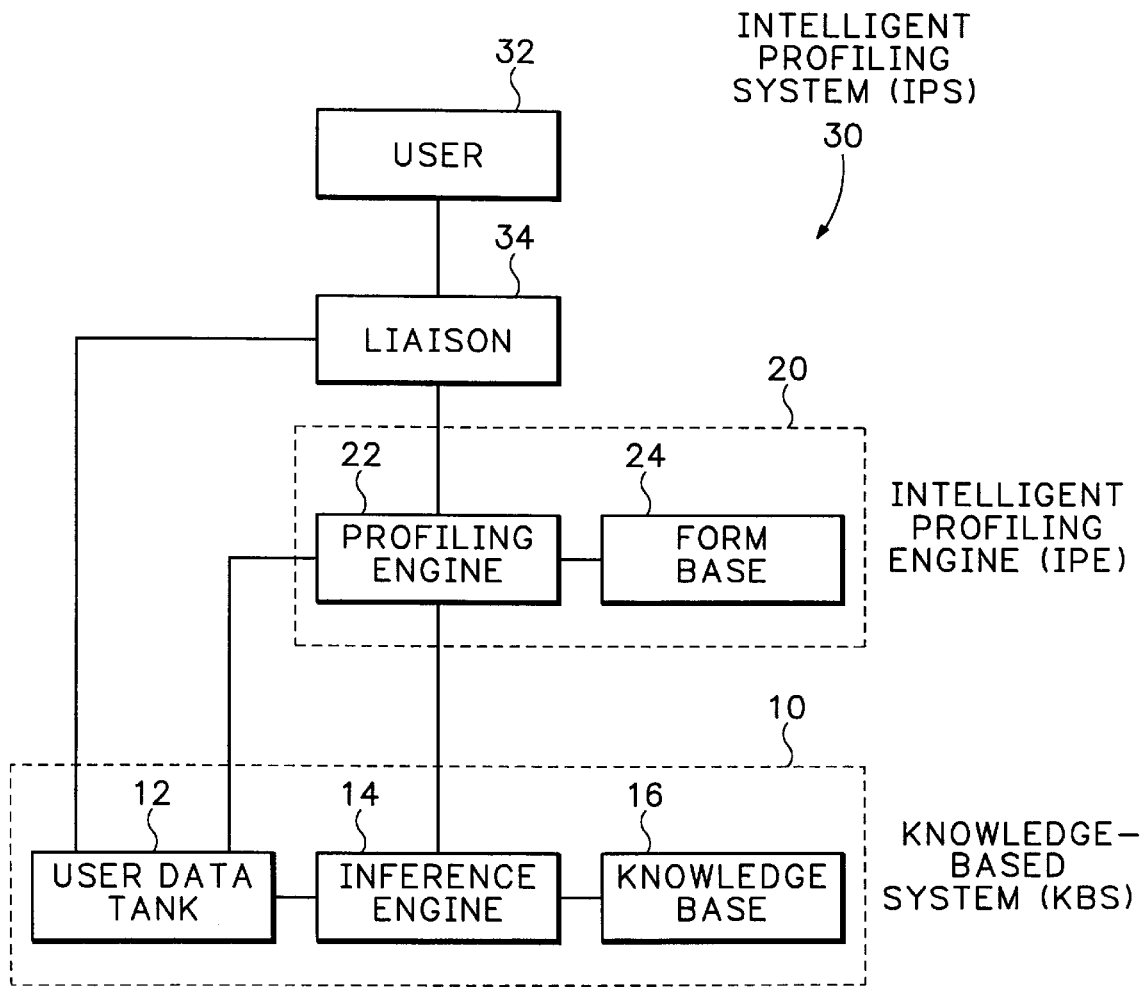

Interview Form for Asthma

1. What type of asthma do you have?    60

☐ Exercise-induced asthma
   ☐ Allergy-induced asthma
   ☐ Occupational asthma
   ☐ Drug-induced
   ☐ Viral-induced
   ☐ Nocturnal asthma 2. How often do you experience daytime asthma symptoms (wheezing, coughing, and breathlessness)?

○ Twice per week or less
   ○ More than twice per week but less than once per day
   ○ Daily (at least once per day)
   ○ Continually (throughout the day)

3. How often do you experience asthma attacks?

○ Twice per month or less
   ○ More than twice per month but less than once per week
   ○ More than once per week but less than once per day
   ○ Daily 4. Which topics related to asthma interest you?

☐ Medication side effects
   ☐ Asthma's effect on other illnesses
   ☐ Symptom management
   ☐ Household, occupational, or environmental allergens
   ☐ Asthma's effect on exercise and physical activities
   ☐ Children and asthma
   ☐ School and work issues
   ☐ New research and developments in asthma
   ☐ Clinical trials
   ☐ Other (specify) [               ]

5. What year were you born?

[    ]

[ Submit Profile ]

FIG.4

Dialog Form for Asthma

*How often did you experience daytime asthma symptoms (coughing, wheezing) on 9/30/97?*

Number of occurrences: ☐

[Submit Profile]     ⬉—70

FIG.5

Form—by—User Matrix     80

| Form | Users |
|---|---|
| form—1 | user—1, user—2, ... |
| form—2 | user—3, ... |
| ... | ... |

When inverted, the form—by—user matrix creates the candidate form lists.

82

Candidate Form Lists user—1: (form—1, ...)

user—2: (form—1, ...)

user—3: (form—2, ...)

FIG.6

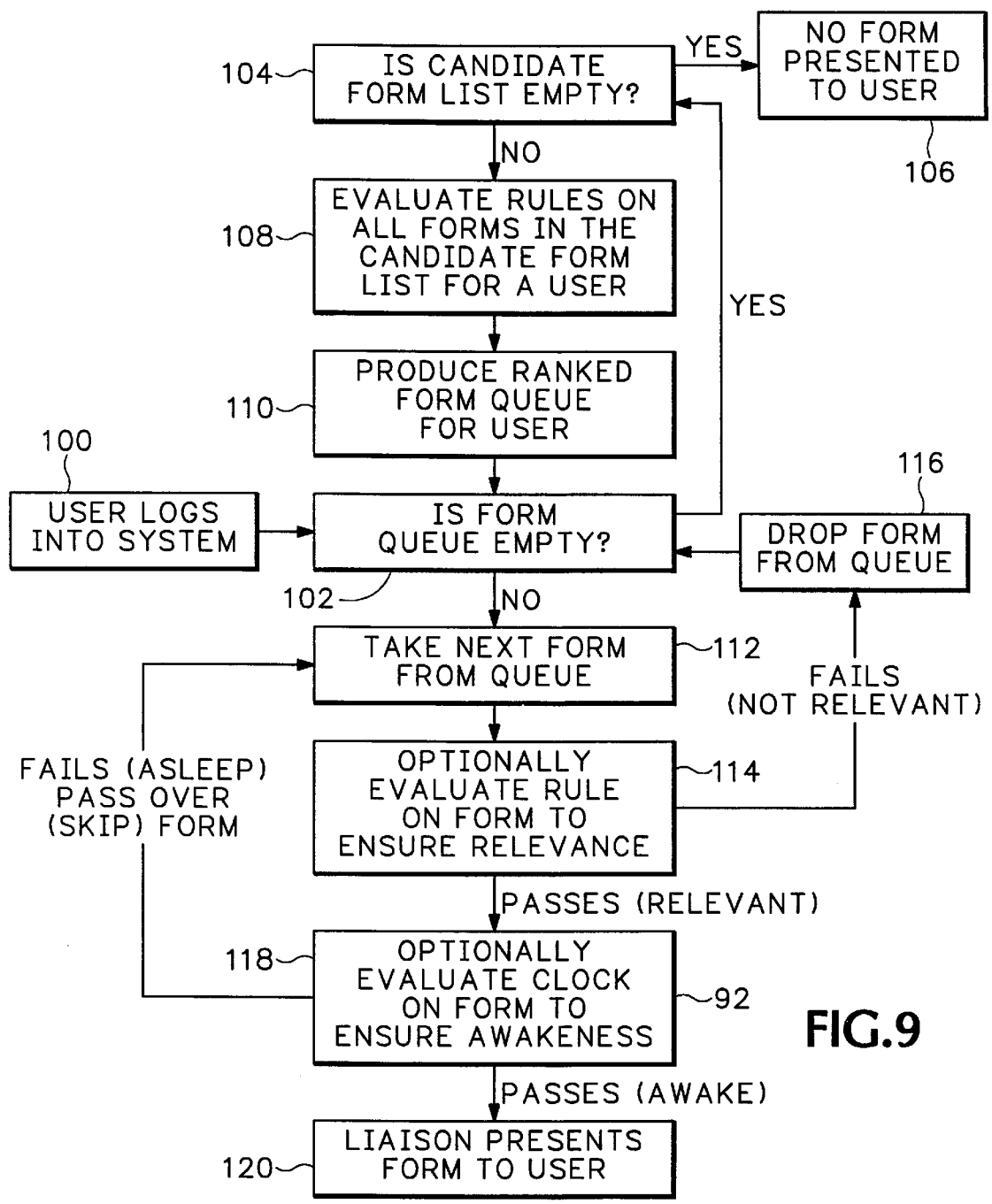

INTELLIGENT PROFILING SYSTEM

This application claims benefit of Provisional Application 60/064,398, filed Oct. 30, 1997.

BACKGROUND OF THE INVENTION

This invention relates to a system that represents and reasons with knowledge to maximize information about users and more particularly to an automated user profiling scheme.

Referring to FIG. 1, a traditional prior art knowledge-based system 10 has three components: a knowledge base 16, a data tank 12, and an inference engine 14. The knowledge base 16 captures concepts and relationships among concepts in a standard symbolic framework. The data tank 12 (often called a "working memory") stores instantiated concepts. For example, the knowledge base 16 represents a concept "temperature" while the data tank 12 stores the fact that the temperature is currently 25 degrees Celsius. The inference engine 14 utilizes the relationships among concepts in the knowledge base 16 and the facts stored in the data tank 12 to reason (make inferences) about the domain covered by the knowledge-based system 10.

A traditional knowledge-based system 10 often operates as an autonomous problem-solving agent. Sometimes, the traditional knowledge-based system 10 is operated by a user, and during the process of reasoning about the domain, an inference engine 14 may ask questions of the user. The particular questions are chosen as a result of the inference engine 14 "blocking" for lack of a particular fact. Hence questions asked of a user are a side effect of lacking information about the domain required to continue the inferencing process.

Thus, a traditional knowledge-based system 10 represents and reasons with knowledge, and it focuses on problem-solving where the user (if present) is merely an adjunct to or resource for the problem-solving process. A traditional knowledge-based system 10 does not focus on a specific goal of gathering extensive information about the user and keeping that information up-to-date (i.e., "user profiling"). Accordingly, a need remains for an automated profiling system that intelligently questions users in order to maximize up-to-date information about them.

SUMMARY OF THE INVENTION

An Intelligent Profiling Engine (IPE) system increases the utility of information collected in user profiles. User profiles are gathered via a question-asking process managed by liaisons. Questions correspond to concepts stored in a knowledge-based system that represents knowledge about particular domains known to be of relevance to users. Questions are presented inside forms chosen by a profiling engine from a form base. This process is referred to as "user profiling" and it entails gathering exhaustive knowledge or grounded information about a user and keeping it up-to-date. Profiling is accomplished by intelligent selection of questions and automated, periodic presentation of those questions to users.

The intelligent profiling system's data collection methodology assumes a communication framework in which users are asked explicit questions by the system and the answers to these questions are stored as "asserted facts" describing the user. These facts make up a "fact space". Users are characterized in fact space according to their asserted facts. Data collection is managed by liaisons, which are persistent objects in the system. Each individual user of the system has a dedicated liaison, which interacts with the user via a graphical user interface. Liaisons present forms containing questions to users, and liaisons store the resulting answers in the user data tank. Liaisons also deliver benefits to users derived from answering questions. The set of all facts asserted by or about a particular user is called a "user profile." In the preferred embodiment, a user profile is similar to a clinical patient record.

The system utilizes knowledge-based artificial intelligence to facilitate classification of information. This knowledge is collected from domain experts and coded into the knowledge-based system utilizing the structure of a domain-specific knowledge model composed of concepts and relations between concepts. Users' answers to questions instantiate knowledge elements as user-asserted facts, which are stored in a user data tank for access by the system. Profiles for users may span multiple domains in the knowledge-based system. In the preferred embodiment, domains of interest include health topics such as breast cancer, asthma, or diabetes, and a user profile may contain facts categorized in multiple domains.

The system performs optimal profiling by applying a series of filters, rules, and clocks against the user data tank, user profiles, and form base. The form base is the repository of all of the forms in the system. A form contains a message, a single question or a set of related questions, along with the answers corresponding to the questions; both questions and answers are derived from concepts in the knowledge base. One or more filters, rules, and clocks together provide a mechanism for targeting forms to sub-populations of users, thus selecting the optimal form to present to a particular user at a particular time. Operations with forms, filters, rules, and clocks are performed by a profiling engine.

The foregoing and other objects, features, and advantages of the invention will become more readily apparent from the following detailed description of a preferred embodiment of the invention, which proceeds with reference to the accompanying drawings.

BRIEF DESCRIPTION OF THE DRAWINGS

FIG. 1 is a schematic diagram of a prior art traditional knowledge-based system.

FIG. 2 is a schematic diagram of an intelligent profiling system according to the invention.

FIG. 4 shows an example interview form stored in a form base shown in FIG. 2.

FIG. 5 shows a dialog form stored in the form base shown in FIG. 2.

FIG. 6 shows a form-by-user matrix and candidate form lists.

FIG. 9 is a step diagram showing operation of rules and clocks used in the intelligent profiling engine shown in FIG. 2.

FIG. 10 shows a message form stored in the form base shown in FIG. 2.

DETAILED DESCRIPTION

Referring to FIG. 2, an Intelligent Profiling System (IPS) 30 performs optimal profiling of a user 32. The IPS 30 is composed of a liaison 34, an intelligent profiling engine (IPE) 20, and a knowledge-based system (KBS) 10, which work together to maximize the utility of information gathered from user 32 over time. The IPS 30 works in combination with an Intelligent Query System described in U.S. patent application Ser. No. 08/936,354 filed Sep. 24, 1997 which is herein incorporated by reference.

Liaisons

A liaison 34 is a persistent object in the system corresponding to a user 32. The liaison 34 delivers various types of forms to user 32 and stores the data gathered from user 32 in a user data tank 12. Liaison 34 also delivers "benefits" of various types to user 32 as a reward for answering questions. Each user 32 has a separate liaison 34.

Figure 3:
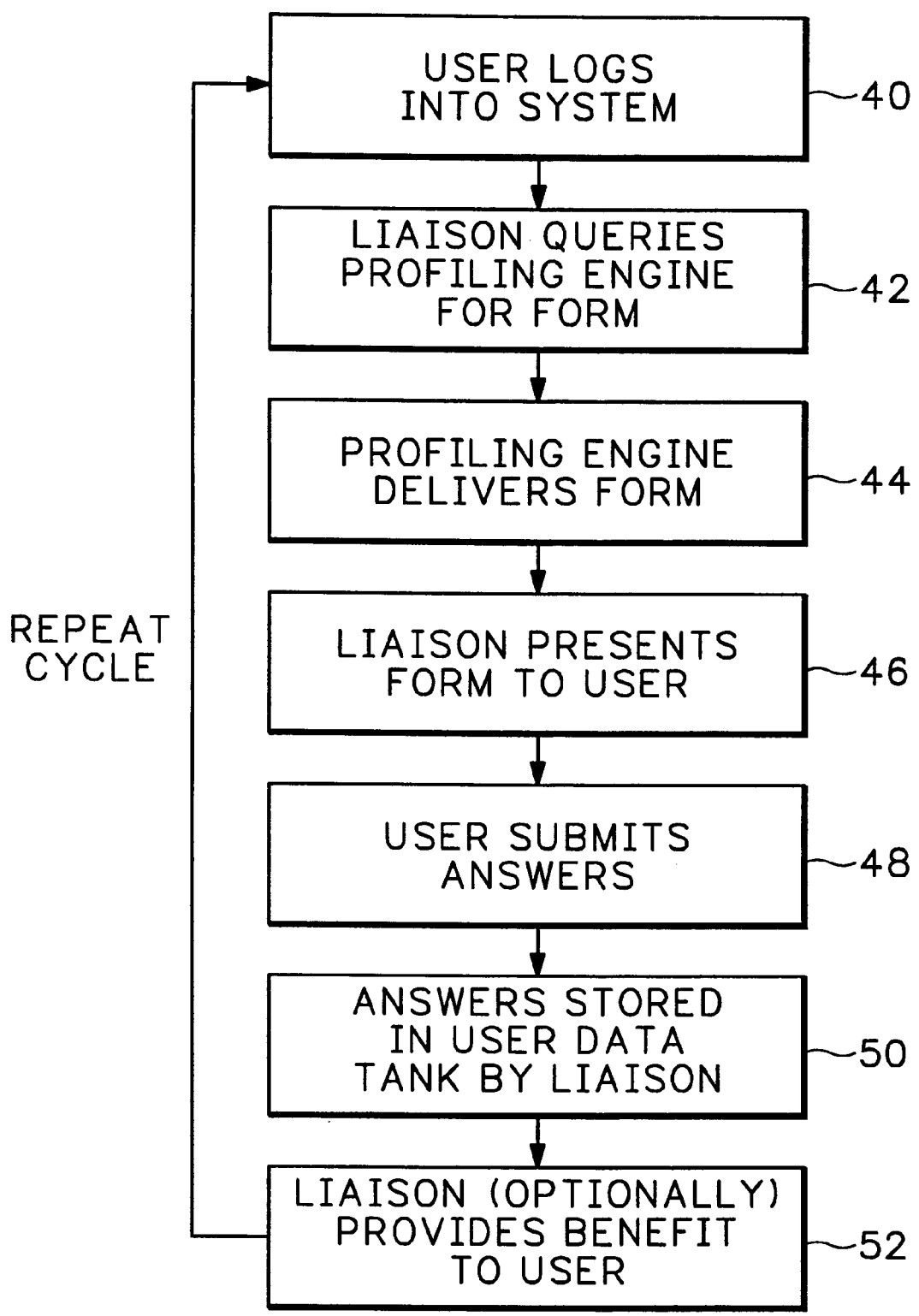
FIG. 3 is a step diagram showing how profiling is done by a liaison shown in FIG. 2.

FIG. 3 shows how user profiling is accomplished. Referring to FIGS. 2 and 3, the process begins in step 40 when a user logs into the IPS system 30. In step 42, the user's liaison 34 queries the profiling engine 20 for a form. In step 44, the profiling engine 20 delivers a particular form from a form base 24 to the liaison 34, which in step 46 presents that form to the user 32. In step 48, the user 32 submits answers to questions contained in the form. Those answers are stored by the liaison 34 in the user data tank 12 in step 50. Finally, in step 52, the liaison 34 may (optionally) provide a benefit to the user 32 as a result of answering the questions in the form to encourage the user 32 to answer further questions in the future. This user profiling cycle is repeated each time a user 32 logs into the IPS system 30 via the World-Wide Web, e-mail, or another communication channel.

Knowledge-Based System (KBS)

Referring back to FIG. 2, the knowledge-based system (KBS) 10 is composed of a user data tank 12, an inference engine 14, and a knowledge base 16.

The user data tank 12 is the repository of all data about each user 32. The user profile for each user 32 contains all the facts about user 32 in user data tank 12. User profiles contain information from multiple domains, and that information is structured by the concepts and relations that make up the knowledge base 16. In other words, the facts in the user data tank 12 are classified according to the structure of the knowledge in the knowledge base 16. The user data tank 12 is a compound, complex data storage mechanism consisting of a collection of object or relational database management systems (DBMSs). Database management systems are known to those skilled in the art and are therefore not described in further detail.

The knowledge base 16 represents concepts and relations between concepts for a particular domain of knowledge in a traditional symbolic framework for knowledge representation. In the preferred embodiment, each domain is a "health topic" such as asthma, diabetes, or breast cancer. A knowledge base 16 is constructed from both manual library research and automated translation of machine-readable databases.

The inference engine 14 performs symbolic reasoning based on the structure of the knowledge base 16 and the data in the user data tank 12. The inference engine 14 operates according to backward-chaining (goal-directed) or forward-chaining (data-driven) algorithms in a traditional framework of inferencing and reasoning. The inference engine 14 performs reasoning to infer additional facts about user 32 at the request of the profiling engine 22 during the process of selecting a form for presentation by liaison 34 to user 32.

KBS 10 thus provides an automated mechanism for translating between the detailed knowledge of the domains describing user 32 and the organization of facts in the user profile for user 32 stored in user data tank 12. For example, KBS 10 translates between a medical domain relevant to user 32 in knowledge base 16 and the space of facts asserted by user 32 in user data tank 12. Thus, KBS 10 makes it possible to map the user-asserted fact, "diagnosed_with_ breast_cancer" to the corresponding concept in the knowledge base 16 and infer additional information about user 32. Knowledge-based systems are known to those skilled in the art and are therefore not described in further detail.

Intelligent Profiling Engine (IPE)

The Intelligent Profiling System (IPS) 30 performs automated and optimal user profiling. There are two primary components to the process of user profiling: a set of forms and a population of users to whom the forms are presented. Form delivery is complicated by the fact that the relationship between users and forms is many-to-many: each form is presented to many users and each user may be the target of many forms. Of particular interest is the Intelligent Profiling Engine (IPE) 20 which employs a series of filters, rules, and clocks for determining which form a user is presented with at any particular time, maximizing the relevance of forms delivered to the user 32. IPE 20 is composed of a form base 24 and a profiling engine 22.

Form Base

The form base 24 is the repository of forms in IPE 20. Forms are presented by liaison 34 to user 32, and user 32 sees a message or one or more questions with sets of answers corresponding to each question. A form also includes a number of other parameters not directly shown to the user. In the preferred embodiment, the list of form parameters includes:

Form ID: Each form requires a name, which is unique within the form base 24.

Filter: Each form optionally has a filter to provide broad identification of the population of users to whom the form should be targeted. A filter defines that population over the fact space of the user data tank 12.

Rule: Each form requires a rule providing a precise (necessary and sufficient) specification of the population of users to whom the form should be targeted. Like a filter, a rule is also defined over the fact space of the user data tank 12; unlike a filter, in determining whether a form should be targeted at a particular user 32, a rule may incorporate additional variables about user 32, for instance, the current context of interaction between user 32 and the IPS system 30.

Questions: Each form requires a message or one or more questions which are specified by the question name, the full question text, and (optionally) a shortened version of the question text.

Answers: Each question requires a corresponding ordered set of answers which are each specified by the answer name, answer text, and answer type. Each answer is linked to a concept in the knowledge base 16 in order that the inference engine 14 can map facts about user 32 to the corresponding concepts in the knowledge base 16.

Persistence: Each form optionally has a persistence value that controls the form clock. The persistence value specifies how long a form stays "awake" and is available for presentation to user 32 once it has initially been presented to user 32 by liaison 34.

Wait-period: Each form optionally has a wait-period value that controls the form clock. The wait-period value specifies how long a form stays "asleep" and is not available for presentation to user 32 following a period of being awake.

Weight: Each form optionally has a weight, a real number between 0 and 1 representing the importance of the form as judged by the human author of the form or by other automated feedback mechanism employed to adapt the form's baseline importance.

Three example forms are presented below: an "interview form", a "dialog form", and a "message form". FIG. 4 shows an example of a five-question interview form 60 which is presented to new users logging into the IPS system 30 for the first time to join a health service for asthma. The interview form 60 represents a mechanism for profiling the user 32 that gathers a number of facts at the time the user 32 joins the health service. The interview form 34 is presented by a liaison 34 to new users via the World-Wide Web, e-mail, or another communication channel. The form parameters for interview form 60 are:

Form ID: "asthma_interview_form"

Filter: None.

Rule: "topic=asthma AND user_status=new_user", which causes the form to be displayed by liaisons to new users interested in the topic of asthma.

Questions: Shown in FIG. 4.

Answers: Shown in FIG. 4.

Persistence: None

Wait-period: None

Weight: None

FIG. 5 shows an example of a one-question dialog form 70 which is presented to users signed up for a health service for asthma. Dialog form 70 represents an ongoing mechanism for profiling an existing user of a health service. Dialog forms can be used to ask "follow-up" questions of a user 32 who has previously answered other questions and provided facts. The dialog form is presented by the liaison 34 to existing users via the World-Wide Web, e-mail, or another communication channel. The form parameters for dialog form 70 are:

Form ID: "asthma_daytime_symptoms_frequency_dialog_form"

Filter: "topic=asthma AND user_status=existing_user", which causes the form to initially be targeted to existing users interested in the topic asthma.

Rule: "experiences_daytime_asthma_symptoms=true", which causes the form to be displayed only if the user has previously asserted that he or she experiences daytime asthma symptoms.

Questions: Shown in FIG. 5.

Answers: Shown in FIG. 5.

Persistence: One day

Wait-period: Zero

Weight: 0.50

FIG. 10 shows an example of a message form 130 which is presented to users signed up for a health service for hepatitis C who have never heard of three treatments: Intron-A, Ro-feron, and Infergen. Message forms represent a mechanism for communicating to the user based on facts known about the user. The message form is presented by a liaison to existing users via the World-Wide Web, e-mail, or another communication channel. When delivered via the World-Wide Web, message forms are analogous to what are commonly called "banner ads." The form parameters for message form 130 are:

Form ID: "hepatitis_c_wondering_about_treatments"

Filter: "topic=hepatitis_c AND user_status=existing_user", which causes the form to initially be targeted to existing users interested in the topic hepatitis C.

Rule: "never_heard_of_intron_a=true OR never_heard_of_roferon=true OR never_heard_of_infergen=true", which causes the form to be displayed only if the user has never heard of one or more of the possible pharmaceutical treatments for hepatitis C.

Questions: Message image

Answers: None

Persistence: Continuous

Wait-period: None

Weight: 0.50

The persistence, wait-period, and weight values are explained in further detail below.

Profiling Engine

Referring back to FIG. 2, the profiling engine 22 chooses the optimal profiling method by utilizing the form base 24, user data tank 12, and inference engine 14. A profiling method includes choice of form and delivery vehicle. The profiling engine 22 utilizes filters, rules, and clocks to choose the form which maximizes the information gathered from user 32; rules executed by the profiling engine 22 may consult the inference engine 14 of KBS 10 to infer facts about user 32 based on the user's profile in user data tank 12. In the following sections, filters, rules, and clocks will be described, followed by a section explaining the complete sequence of operation of the profiling engine 22.

Filters

Each form optionally has associated with it a filter. The purpose of a filter is to reduce the complexity of computation otherwise required for an exhaustive execution of every rule for every user. Filters are executed on a periodic basis to produce a set of candidate users who become targets for each form. Filters are "form-centric" in that they are executed for each active form. Filter execution takes place "off-line" or independent of which users may be logged into the system.

A filter provides a specification in fact space of a target population of users (the "test") and the profiling engine 22 applies the test to the existing population of users to construct a list of those users for whom the particular form is applicable. Referring to FIG. 6, the result of applying the test to all users is a form-by-user matrix 80 that contains, for each form, a list of users for whom that form is applicable. The form-by-user matrix 80 is then inverted to create a series of candidate form lists 82, which contain, for each user 32, the forms applicable to that user. Thus, the filter reduces the universe of all possible forms to a smaller list of forms applicable to each user. This in turn reduces the number of rules that must be executed when the user 32 logs into the system, as will be described below. The use of filters is optional in the system.

For example, a form base containing 100 forms distributed equally among 10 health topics would have 10 forms applicable to users interested in the topic asthma. Of those 10 forms, only five might be applicable to existing users. Hence the filter:

Filter: "topic=asthma AND user_status=existing_user" provides a 20:1 reduction in the number of form rules that must be executed by the system when the user 32 interested in asthma logs into the IPS system 30. Filters are optional because such a 20:1 reduction in complexity is not important if the system is supporting only a small population of users. However, as the IPS system 30 scales to support a very large population of users, maintaining consistent system performance requires the decrease in complexity provided by filters.

Rules

Each form always has associated with it a rule. The purpose of a rule is to produce a ranking which represents how important it is that the form be asked of a particular user at a particular point in time. Referring back to FIG. 2, rules may consult the inference engine 14 of KBS 10 as part of this process. Because multiple forms are competing to be presented, a rule provides a mechanism to select the form that will optimize the quality or amount of information gathered, incorporating (if present) the form weight parameter described earlier. In the preferred embodiment, rules are executed on a periodic basis to construct a "form queue" that ranks applicable forms for user 32. Also, immediately before any form is presented to user 32, its rule is re-executed to ensure the applicability of the form at that particular time. Rules are "user-centric" in that they are executed on demand for each active user.

A form's rule takes as input the user profile for user 32 and produces an assessment of the importance of the form 70 with respect to user 32. In its simplest manifestation, a rule is composed of a necessary and sufficient specification in fact space of a target population of users (the "test") and a real-valued parameter (the form weight). The profiling engine 22 applies the test to the user profile for user 32 to determine if the form is applicable to user 32; if the form is applicable, the form weight value is utilized to calculate the importance of the form to user 32. For example, a simple rule is:

Rule: "experiences_daytime_asthma_symptoms=true".

This rule causes the form 70 to be displayed only if the user 32 has previously asserted that he or she experiences daytime asthma symptoms. If the form 70 has a filter, then the rule test is applied to only that subset of the population of users identified by the filter to be candidates for the form, as represented in the form-by-user matrix 80 in FIG. 6.

Sophisticated rules can also be constructed. For example, in addition to the form weight parameter, rules can incorporate the form "completeness." Consider the rule:

Rule: "IF topic=asthma AND user_status=existing_user
 THEN importance=weight*(1.00−completeness)"

If a form had already been presented to and answered by user 32 (as determined by the presence of a particular fact for user 32 in user data tank 12), the above rule would scale the weight of the form by a factor calculated from the degree of completeness. If a user provided 30% of the expected number of answers to the questions in a form, the form weight parameter would be scaled by 0.70 (calculated as 1.00 minus the degree of completeness: 0.30). This type of completeness-based rule modifies the importance of a form (and thus the likelihood that the form will be presented to user 32 by liaison 34) based on how completely the facts known about user 32 answer the questions contained in the form. In other words, if none of the facts solicited by the form are known about user 32, it is more important to present the form to user 32, whereas if some or all of the facts solicited by the form are known about user 32, it is less (or not at all) important to present the form to user 32. In this way, IPS 30 intelligently profiles users based on the current state of knowledge about them.

A second example of a sophisticated rule could incorporate context information about which part of the system 30 the user 32 is interacting with. For example, rules can incorporate the "location" of the user 32 in the graphical user interface (not shown). Here is a rule for a form containing questions about treatments for asthma:

Rule: "IF topic=asthma AND user_status=existing_user
 AND current_article_type=treatment
 THEN importance=1.00
 ELSE importance=0.00"

If user 32 is currently reading an article about treatments for asthma, then the importance of the form asking questions about treatments for asthma would be 1.00. In other words, if the context of what user 32 is doing in the system 30 coincides with the questions in a form (as determined by the form's rule), it is more important to present that form to user 32, whereas if the context of what user 32 is doing in the system 30 is unrelated to the questions in the form, it is less (or not at all) important to present the form to user 32. In this way, IPS 30 intelligently profiles users based on the context of their activity in the system.

A third example of a sophisticated rule is one that utilizes the inference engine 14 of KBS 10 as part of the process of identifying the target population of users for the form. For example, rules can request the profiling engine 22 to utilize the inference engine 14 during rule execution. Here is a rule for a form to be presented to users with occupational asthma:

Rule: "asthma_type=occupational AND use_inference_
 engine=true"

If user 32 had not yet identified the type of his or her asthma but had already asserted the fact "employed_by=sawmill", and the inference engine 14 was able to utilize the knowledge base 16 to infer that "asthma_type=occupational", this rule would be triggered. In other words, KBS 10 can be utilized to infer additional facts about user 32, which may characterize user 32 in ways that increase the importance of particular forms. In this way, IPS 30 intelligently profiles users by utilizing the symbolic reasoning capabilities of KBS 10.

Clocks

Each form has associated with it a clock. The purpose of the clock is to control the "user experience" so that if user 32 is presented with a form via the graphical user interface and chooses not to answer the questions in the form, the same form persists for some period of time after which it is replaced by a different form. The clock enables the system 30 to keep track of how long the form should persist in an "awake" state and be presentable to user 32 and also how long the form should then wait in an "asleep" state and not be presented to user 32. After the waiting period has passed, the clock enables the system to reawaken the form again.

Figure 7:
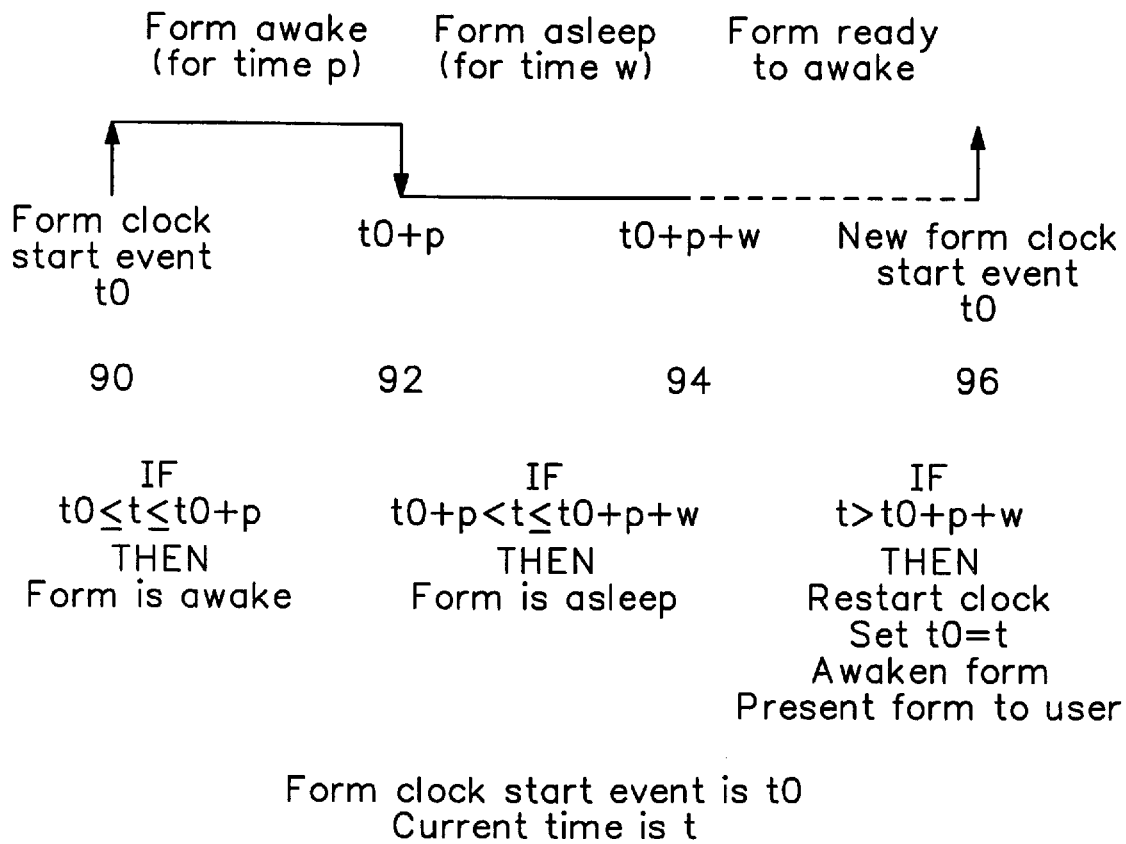
FIG. 7 shows the wake/sleep clock cycle of a form.

A clock utilizes the persistence and wait-period values for a form, combined with the last clock start event of the form for the user 32, to determine the state of the form: awake or asleep. Because clock start events are stored separately for each form for each user 32, a particular form may be awake for some users and asleep for other users at any given time. Only forms, that are awake, are eligible to be presented to a user. The wake/sleep cycle for a form is shown in FIG. 7.

For example, assume the persistence for a dialog form is two days (p=2) and the wait-period is thirty days (w=30). The form clock start event 90 occurs when the form is first presented to the user 32 and is defined as time t0. Let t0 be Oct. 23, 1997, the date the dialog form is presented to the user 32. Then, while the current time is between Oct. 23, 1997 (t0) and Oct. 25, 1997 (t0+p), the form will persist and continue to be eligible to be presented to the user 32. Once the current time passes Oct. 25, 1997 (t0+p) 92, until the current time reaches Nov. 22, 1997 (t0+p+w) 94, the form is asleep and not eligible to be presented to the user 32. After Nov. 22, 1997, the form is ready to be awakened when another form clock start event occurs 96 (i.e., when the form is judged to be important enough to be presented to the user again). Thus, the form clock enables the system 30 to provide the user experience, "Given that a dialog form is deemed (and remains) the most relevant, ask that dialog form for two days, then don't ask it again for a month." In this way, IPS 30 intelligently profiles users by persisting in the action to collect relevant information, yet accommodating an appropriate user experience.

Operation of the Profiling Engine

Referring back to FIG. 2, the profiling engine 22 provides a mechanism to intelligently select the most relevant form in form base 24. For the most basic forms, the profiling engine 22 simply executes form rules against user profiles from user data tank 12 to determine the most relevant form to be presented to user 32. For the most sophisticated forms, the profiling engine 22 utilizes filters, rules, clocks, and reasoning assistance from the inference engine 14 to process user profiles from user data tank 12 to select the most important form to present to user 32.

Figure 8:
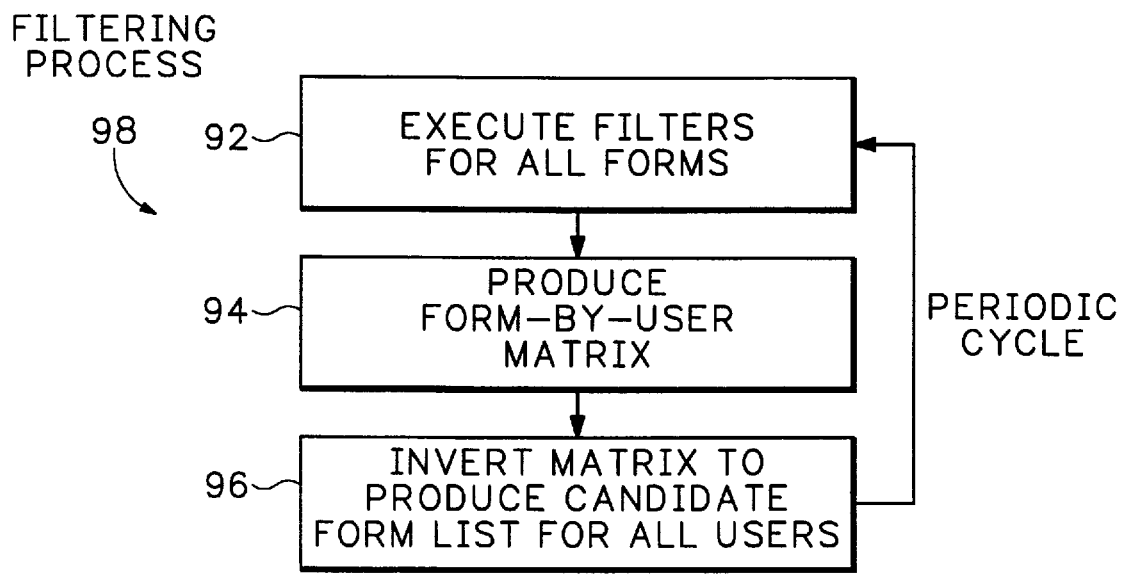
FIG. 8 is a step diagram showing operation of filters used in the intelligent profiling engine shown in FIG. 2.

FIG. 8 illustrates the filtering process 98: one phase of operation for profiling engine 22 (FIG. 2). Recall the purpose of filters is to reduce the complexity of computation otherwise required for an exhaustive execution of every rule for every user. The filtering process 98 is executed on a periodic basis by the profiling engine 22 (FIG. 2) to produce a set of candidate users who become targets for each form. In step 93, filters for all forms are executed. As described earlier, the result of applying all filters to the population of users is a form-by-user matrix 80 (FIG. 6), which is produced in step 95. Finally, in step 97, the form-by-user-matrix 80 is inverted to produce candidate form lists 82 (FIG. 6) for all users. The candidate form lists 82 are stored in user data tank 12 (FIG. 2) for later use by the system 30. In this way, execution of filters by the profiling engine 22 on a periodic cycle reduces the number of forms applicable to each user 32, thereby reducing the number of rules that must be executed by the profiling engine 22 when the user 32 logs into the system 30.

FIG. 9 illustrates how rules and clocks are utilized by the profiling engine 22 (FIG. 2). The result of the process described in FIG. 9 will be the selection of the most relevant form to be presented to the user 32. In step 100, the user 32 logs into the system 30, which initiates this process. In step 102, the profiling engine 22 checks the user's form queue to see if it is empty (which it will be for a new user). If the form queue is empty for the user 32, the profiling engine 22 checks the candidate form list 82 (FIG. 6) for the user to see if the candidate form list 82 is empty. Recall that the candidate form list 82 is refreshed on a periodic cycle by the filtering process 98 (FIG. 8). If the candidate form list 82 is empty, it means that the filtering process 98 found no forms applicable to the user 32, so no form will be presented to the user 32. The next time the user 32 logs into the system 30, the same process will be invoked because a later cycle of the filtering process 98 may have identified forms applicable to the user 32.

If in step 104 the candidate form list 82 (FIG. 6) is not empty, then the profiling engine 22 (FIG. 2) loops through the forms in the candidate form list 82 to evaluate each form's rule in step 108. Execution of each rule will return an importance value for that form with respect to that user 32, as described earlier. Hence the result of step 108 is a list of importance values for each form in the candidate form list 82 for that user. The list of importance values is sorted to create the "form queue" in step 110. The form queue is thus an ordered list of forms ranked by importance for the user 32. Because each user's profile can be different, each user can have a different form queue identifying the most relevant forms for that user.

In step 102 now, the form queue is not empty, so the profiling engine 22 (FIG. 2) proceeds to step 112 and takes the next (top) form from the form queue. In step 114, the rule for the top-ranked form is optionally evaluated again to ensure the form is still relevant. Step 114 is required only if the form queue is stored persistently in user data tank 12 (FIG. 2) because the importance values in the form queue could become obsolete if the user 32 adds information to his or her user profile or if the continued elapsing of time causes forms in the form queue to fall asleep with respect to any form clock start events.

If in step 114, execution of the top-ranked form's rule indicates the form is no longer relevant to the user, the form is removed from the form queue in step 116 and the profiling engine 22 returns to step 102. If execution of the top-ranked form's rule verifies the relevance of the form to the user 32, then the profiling engine 22 executes step 118. In step 118, the form clock is optionally checked to ensure the form is still awake. Step 118 is optional because simpler forms do not have persistence and wait-period values, and hence have no form clocks: they are always awake.

Forms with persistence and wait-period values follow a wake/sleep cycle as described earlier in FIG. 7. If the top-ranked form's clock indicates the form has fallen asleep, the form is passed over (skipped) and the profiling engine 22 returns to step 112 and takes the next form from the form queue. If the top-ranked form is still awake, it is passed by the profiling engine 22 to the user's liaison 34, which presents the form to the user 32.

Thus, the profiling engine 22 (FIG. 2) demonstrates an automated profiling system that intelligently questions users via forms which are selected based on their importance with respect to the user profile and the dynamics of user interaction with the system. This process maximizes up-to-date information known about the users by the system.

Having described and illustrated the principles of the invention in a preferred embodiment thereof, it should be apparent that the invention can be modified in arrangement and detail without departing from such principles. I claim all modifications and variation coming within the spirit and scope of the following claims.

What is claimed is:

1. An intelligent profiling system, comprising:

user data tanks retaining facts about profiling system users;

multiple forms having a topic identifier for one or more questions and associated rules linking the facts about the users to the topic identifiers for the forms, the forms including different selectable weighting factors that automatically vary the importance of the forms according to user status in the intelligent profiling system and what context of information the user is currently accessing in the intelligent profiling system;

a form base retaining the multiple forms; and an intelligent profiling engine selecting forms in the form base most relevant to the users and presenting the selected forms to the users according to the facts about the users and the rules associated with the forms.

2. A system according to claim 1 wherein one of the different selectable weighting factors comprises a completeness factor that varies for individual forms according to a percentage of questions in the individual forms answered by the users.

3. A system according to claim 1 wherein one of the selectable weighting factors varies according to the context of information the users are currently accessing in the profiling system and how related the context of that information is to the questions in the forms.

4. A system according to claim 1 including a liaison automatically querying the profiling engine for forms, presenting the forms to the users and storing answers by the users to the forms as facts in the user data tank.

5. A system according to claim 1 including a knowledge based system used by the profiling engine for selecting which forms to present to the users.

6. A system according to claim 5 wherein the knowledge based system includes the following:
   a knowledge base storing concepts and relationships between concepts for a particular domain of knowledge; and
   an inference engine mapping the user asserted facts in the user data tanks to the concepts in the knowledge base, the inference engine selectably enabled and disabled according to the rules associated with the forms.

7. An intelligent profiling system, comprising:
   user data tanks retaining facts about profiling system users;
   multiple forms having a topic identifier for one or more questions and associated rules linking the facts about the users to the topic identifiers for the forms;
   a form base retaining the multiple forms;
   an intelligent profiling engine selecting forms in the form base most relevant to the users and presenting the selected forms to the users according to the facts about the users and the rules associated with the forms; and
   filters that produce lists of forms most applicable to each one of the users, the profiling engine using the rules in combination with the filters to select the forms presented to each one of the users.

8. An intelligent profiling system, comprising:
   user data tanks retaining facts about profiling system users;
   multiple forms having a topic identifier for one or more questions and associated rules linking the facts about the users to the topic identifiers for the forms wherein the forms each include a clock parameter that determines how often the forms are presented to the users by the profiling engine;
   a form base retaining the multiple forms; and
   an intelligent profiling engine selecting forms in the form base most relevant to the users and presenting the selected forms to the users according to the facts about the users and the rules associated with the forms.

9. A system according to claim 8 wherein the clock parameter determines how often the forms are eligible for presentation to the users and how long the forms are ineligible for presentation to the users.

10. An intelligent profiling system, comprising:
    user data tanks retaining facts about profiling system users;
    multiple forms having a topic identifier for one or more questions and associated rules linking the facts about the users to the topic identifiers for the forms;
    a form base retaining the multiple forms; and
    an intelligent profiling engine selecting forms in the form base most relevant to the users and presenting the selected forms to the users according to the facts about the users and the rules associated with the forms;
    a liaison automatically querying the profiling engine for forms, presenting the forms to the users and storing answers by the users to the forms as facts in the user data tank, wherein the liaison provides incentives to the users to answer a maximum number of the questions in the forms.

11. An intelligent profiling system according to claim 10 wherein the incentives comprise banner ads.

12. A method for profiling users in an automated user profiling system, comprising:
    generating multiple forms each having one or more questions about associated topics; storing the multiple forms;
    retaining user facts from the users answering the questions in the forms;
    associating rules with each one of the multiple forms, the rules linking the user facts to the topics of the questions in the forms; and
    selecting forms most relevant to present to the users according to the user facts, the rules associated with the forms and a weighting factor that varies the importance of individual forms according to a percentage of the questions in the individual forms answered by users.

13. A method according to claim 12 including the following:
    associating clocks with at least some of the forms checking whether the clocks with forms indicate the forms are awake; presenting the forms in the form queue identified as being awake; and skipping presentation of forms having clocks indicating the forms as asleep.

14. A method for profiling users in an automated user profiling system, comprising:
    generating multiple forms each having one or more questions about associated topics; storing the multiple forms;
    retaining user facts from the users answering the questions in the forms;
    associating rules with each one of the multiple forms, the rules linking the user facts to the topics of the questions in the forms;
    selecting forms most relevant to present to the users according to the user facts and the rules associated with the forms;
    generating filters for the multiple forms that associate categories of topics associated with the forms to the users;
    periodically applying the filters to the forms to generate a form-by-user matrix that lists the relevant users for the forms;
    inverting the form-by-user matrix to generate candidate form lists for the users; and
    presenting the forms to the users according to the candidate form lists.

15. A method according to claim 14 including the following:
    checking the candidate form lists for the users;
    executing the rules associated with the forms in the candidate form lists, the executed rules generating importance values for the forms with respect to the users;

ranking the forms in the candidate form list according to the importance values;

storing the ranked forms in form queues; and presenting the forms to the users according to the ranked order in the form queues.

16. A method according to claim 15 including the following:

evaluating the rules associated with the forms stored in the form queue;

removing forms in the form queue that are no longer indicated as relevant by the evaluated rules; and presenting the forms in the form queue that are indicated as still relevant to the user.

17. A method according to claim 16 wherein evaluating the rules comprise the following:

checking whether forms having clocks are awake;

presenting the forms in the form queue identified as being awake; and skipping presentation of forms identified as asleep.

18. A method according to claim 16 including the following:

presenting forms to the user that exist in the user form queue;

checking the candidate form list when the user form queue is empty;

ranking the forms in the candidate form list according to the importance values;

presenting the forms in the order of the ranked candidate form to the user; and presenting no forms to the user when there are no forms in the candidate form list or the user form queue.

19. Forms presented to a user in an intelligent profiling system, the forms comprising:

a form ID identifying a topic associated with the form;

one or more questions used for retrieving facts asserted by the user in response to the questions;

a rule linking the asserted facts to the form ID, the forms presented to the user according to the rules that identify the relevance between the facts asserted by the user and the topics associated with the forms; and selectable weighting factors that are applied to vary the importance of the forms according to the context of information the user is currently accessing in the intelligent profiling system and how similar the context of information is to the questions in the forms.

20. Forms according to claim 18 wherein at least some of the forms include banner messages that vary according to user responses to questions in the forms and the context of information the user is currently accessing.

21. A system for presenting forms to a user in an intelligent profiling system, the forms comprising:

a form ID identifying a topic associated with the form;

one or more questions used for retrieving facts asserted by the user in response to the questions; and a rule linking the asserted facts to the form ID, the forms presented to the user according to the rules that identify the relevance between the facts asserted by the user and the topics associated with the forms; and filters comprising lists of forms most applicable to each one of the users, the rules in combination with the filters determining which forms are presented to the user.

22. Forms according to claim 21 including a weight parameter that indicates the importance of the rules.

23. Forms according to claim 22 including a location factor that varies the weight parameter according to what information the user is currently accessing in the profiling system.

24. Forms presented to a user in an intelligent profiling system, the forms comprising:

a form ID identifying topics associated with the forms;

one or more questions used for retrieving facts asserted by the user in response to the questions; and a rule linking the asserted facts to the form ID, the forms presented to the user according to the rules that identify the relevance between the facts asserted by the user and the topics associated with the forms, wherein the forms include a completeness factor that varies the weight parameter for individual forms according to a percentage of questions in the individual forms answered by the users.

25. Forms presented to a user in an intelligent profiling system, the forms comprising:

a form ID identifying a topic associated with the forms;

one or more questions used for retrieving facts asserted by the user in response to the questions;

a rule linking the asserted facts to the form ID, the forms presented to the user according to the rules that identify the relevance between the facts asserted by the user and the topics associated with the forms; and a clock parameter that determines how long and how often the forms should be presented to the user.

26. Forms presented to a user in an intelligent profiling system, the forms comprising:

a form ID identifying a topic associated with the form;

one or more questions used for retrieving facts asserted by the user in response to the questions; and a rule linking the asserted facts to the form ID, the forms presented to the user according to the rules that identify the relevance between the facts asserted by the user and the topics associated with the forms, wherein the forms comprise banner ads.

* * * * *